United States Patent [19]

Lam

[11] Patent Number: 6,068,646

[45] Date of Patent: May 30, 2000

[54] ARTERY CLAMP

[76] Inventor: Anthony Lam, 1015-74 Street N.W., Edmonton, Alberta, Canada, T6A 2X8

[21] Appl. No.: 09/217,598

[22] Filed: Dec. 21, 1998

[30] Foreign Application Priority Data

Nov. 27, 1998 [CA] Canada ................................. 2254589

[51] Int. Cl.[7] .................................................. A61B 17/00
[52] U.S. Cl. .......................................... 606/203; 606/157
[58] Field of Search ..................... 606/201, 202, 606/203, 157, 151, 213

[56] References Cited

U.S. PATENT DOCUMENTS

| | | | |
|---|---|---|---|
| 1,281,653 | 10/1918 | Plummer | 606/203 |
| 1,322,050 | 11/1919 | Plummer | 606/203 |
| 3,884,240 | 5/1975 | Gilman | 128/325 |
| 4,557,262 | 12/1985 | Snow | 128/325 |
| 4,760,846 | 8/1988 | Mers Kelly et al. | 128/327 |
| 4,957,105 | 9/1990 | Kurth | 128/96.1 |
| 5,295,996 | 3/1994 | Blair | 606/203 |
| 5,304,186 | 4/1994 | Semler et al. | 606/151 |
| 5,304,201 | 4/1994 | Rice | 606/201 |
| 5,307,811 | 5/1994 | Sigwart et al. | 128/677 |
| 5,591,201 | 1/1997 | Lam | 606/201 |
| 5,601,596 | 2/1997 | Lam | 606/201 |
| 5,601,597 | 2/1997 | Arrowood et al. | 606/203 |
| 5,643,315 | 7/1997 | Daneshvar | 606/201 |
| 5,728,120 | 3/1998 | Shani et al. | 606/201 |

*Primary Examiner*—Michael Buiz
*Assistant Examiner*—Kevin Truong
*Attorney, Agent, or Firm*—Christensen O'Connor Johnson & Kindness PLLC

[57] ABSTRACT

An artery clamp includes an inelastic girth band having an interior face and an exterior face. The band is secured about a limb. A plunger extends through the band. The plunger has a first end extending past the interior face and a second end extending past the exterior face. A pressure member mounted on the first end of the plunger. Pressure is exerted with the plunger and then the plunger is locked in a selected position in relation to the band.

15 Claims, 5 Drawing Sheets

ARTERY CLAMP

FIELD OF THE INVENTION

The present invention relates to an artery clamp and, in particular, an artery clamping band.

BACKGROUND OF THE INVENTION

There are a number of artery clamps that are in the form of bands that wrap around a limb of a patient. One example of such an artery clamp is U.S. Pat. No. 4,760,846 which issued to Mers Kelly et al. in 1988. The Mers Kelly reference discloses a pressure member mounted on a band. The tighter the band member is secured to the limb of the patient, the greater the clamping force exerted upon the artery by the pressure member. Another example of such an artery clamp is U.S. Pat. No. 5,295,996 which issued to Blair in 1994. The Blair reference discloses a semi-spherical pressure member mounted on a band. In one embodiment, the semi-spherical pressure member has a spring that can be preadjusted to control the amount of pressure applied. In another embodiment, a pulse indicator rod is built into the pressure member. Pulsing of the artery effects pulsing of the indicator rod.

Artery clamping bands are a convenient way of applying arterial pressure. The problem with the arterial clamping bands, as described above, is that they are not sensitive enough for use in the applications for which they would otherwise be best suited. The pressure is controlled primarily by how tightly the band is secured to the patient's limb.

SUMMARY OF THE INVENTION

What is required is an artery clamp band that attaches to a limb by means of a band and has enhanced pressure control.

According to the present invention there is provided an artery clamp which includes an inelastic girth band having an interior face and an exterior face. Means is provided for cinching the band about a limb. A plunger extends through the band. The plunger has a first end extending past the interior face and a second end extending past the exterior face. A pressure member is mounted on the first end of the plunger. Means is provided for locking the plunger in a selected position in relation to the band.

With the artery clamp, as described above, the plunger is used as the means for exerting pressure upon an artery. The artery clamp is not dependent for its operation on the tightness of the band about the patient's limb. In fact, it is preferred that the band be secured about the patient's limb, without applying a compressive force, so that any force applied is localized to the area of the plunger. Medical staff pressing on the plunger can use finger control and are better able to gauge the amount of force which is being applied. The preferred means for locking the plunger in a selected position includes a movable locking member having a free position spaced from the plunger and leaving the plunger free to move and a locking position engaging the plunger and thereby lock the plunger in position.

Although beneficial results may be obtained through the use of the artery clamp, as described above, once the artery clamp is in position it is desirable that provision be made for fine adjustments to incrementally increase or decrease pressure. Even more beneficial results may, therefore, be obtained when the plunger is rotatable in relation to the band and the plunger has a helically threaded portion. The movable locking member is also provided with a threaded portion. The threaded portion of the movable locking member engages the helically threaded portion of the plunger when in the locking position. Fine pressure adjustment can then be effected by rotation of the plunger to move the plunger in relation to the movable locking member along an inclined plane provided by the helically threaded portion.

Although beneficial results may be obtained through the use of the artery clamp, as described above, constructing a movable locking member that is suitable for use on a band can be a problem. Even more beneficial results may, therefore, be obtained when the movable locking member has a body with an elongate aperture through which the plunger extends. In the locking position a sidewall of the aperture of the movable locking body engages the plunger.

Although beneficial results may be obtained through the use of the artery clamp, as described above, it is essential that when the movable locking member is placed in the locking position it stays there. Even more beneficial results may, therefore, be obtained when a locking member housing is provided having a cavity with a first interior surface and a second interior surface. Each of the first interior surface and the second interior surface has a first engagement means and a second engagement means. The body of the locking member has a first face and a second face. Each of the first face and the second face has mating engagement means adapted to mate with one of the first engagement means and the second engagement means. When the movable locking member is in the free position the mating engagement means mates with the first engagement means and when the movable locking member is in the locking position the mating engagement means mates with the second engagement means.

There are a variety of means of securing the band about a patient's limb. Two ways are illustrated in the Mers Kelly reference and the Blair references discussed about. The preferred manner of securing the band is to provide an adhesive area on the exterior face of the band that is covered by a tear away covering. The tear away covering is torn away and the band overlapped until an interior face of one portion of the band adheres to the adhesive area.

Although beneficial results may be obtained through the use of the artery clamp, as described above, through repeated use the required depth for the plunger in order to stop bleeding is learned for different applications. Even more beneficial results may, therefore, be obtained when visual depth indicator markings are positioned on the plunger. This enables experienced medical staff to rapidly position the plunger at the required depth.

According to another aspect of the invention there is provided a method of stopping the flow of blood through an artery. A first step involves providing an artery clamp as described above. A second step involves securing the inelastic girth band about a limb of a patient. A third step involves depressing the plunger to exert pressure upon an artery of a patient. A fourth step involves locking the plunger in a selected position once the flow of blood through the artery has been stopped.

The method, as described above, represents a radical departure from the method of use of prior art artery clamping bands. In the prior art the tightness of the band determined the pressure exerted. With the present method, the band is positioned around a person's wrist without applying a compressive once. The band, therefore, merely serves as a mounting for the plunger. It is the plunger which actually exerts the required force. This method enables much improved pressure control. This pressure control can be even further improved with the addition of means for a fine adjustment, such as a plunger with helical threads as will hereinafter be further described.

BRIEF DESCRIPTION OF THE DRAWINGS

These arid other features of the invention will become more apparent from the following description in which reference is made to the appended drawings, wherein.

DETAILED DESCRIPTION OF THE PREFERRED EMBODIMENT

Figure 1:
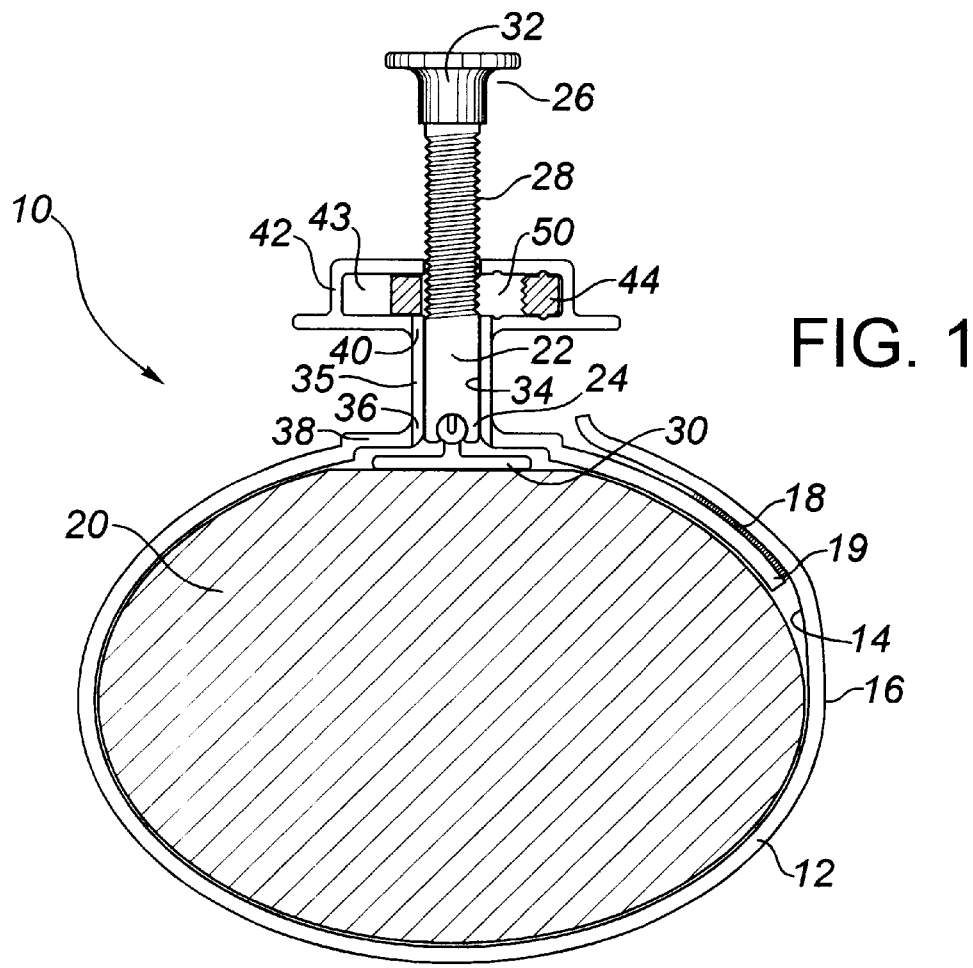
FIG. 1. is a front elevation view, in section, of an artery clamp constructed in accordance with the teachings of the present invention, with a locking member in a first or free position.

The preferred embodiment, an artery clamp generally identified by reference numeral 10, will now be described with reference to FIGS. 1 through 8.

Figure 4:
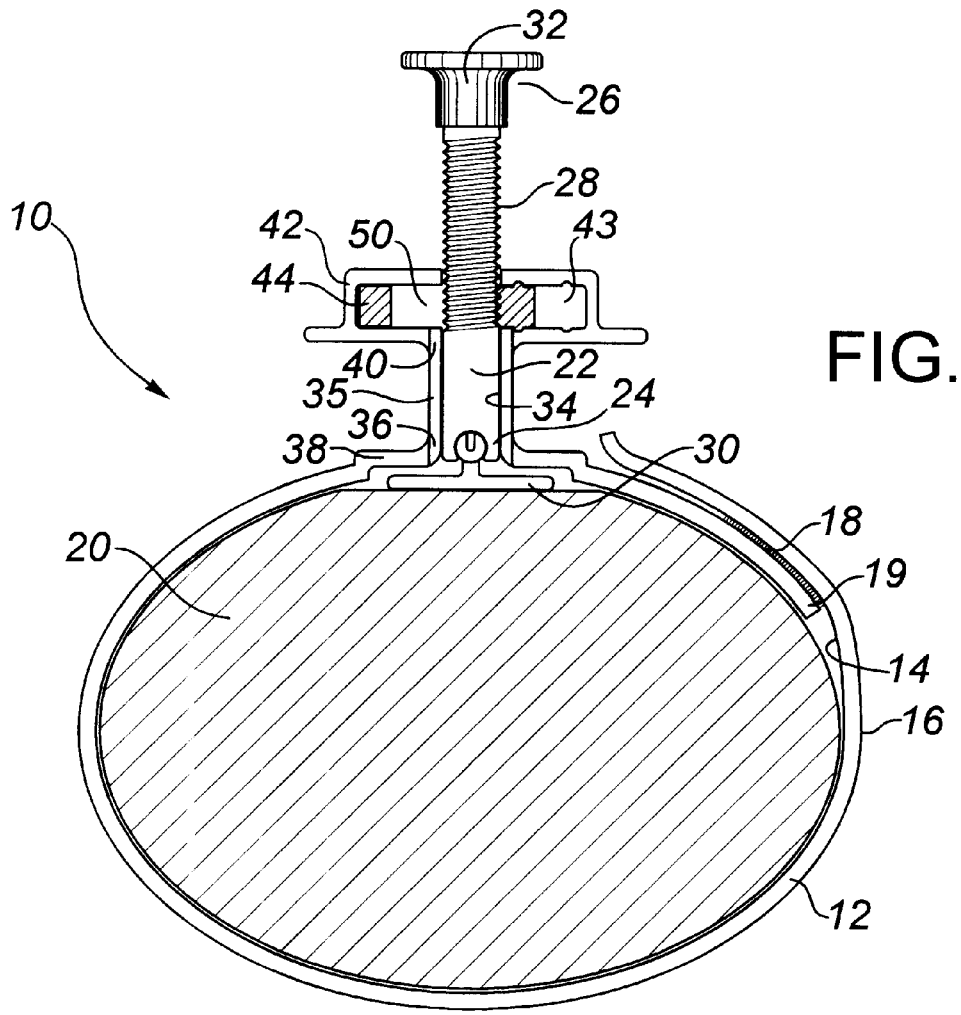
FIG. 4 is a front elevation view, in section, of the artery clamp illustrated in FIG. 1, with the locking member in a second or locking position.
Figure 7:
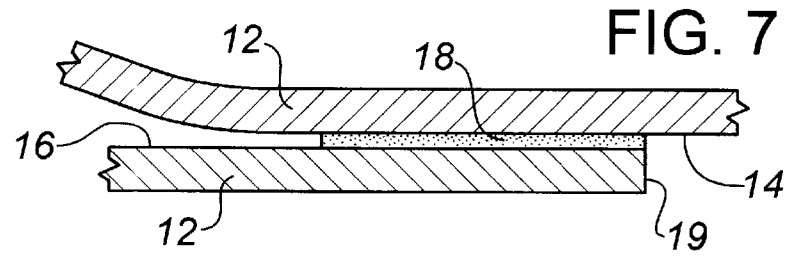
FIG. 7 is a detailed front elevation view, in section, of a band attachment for the artery clamp illustrated in FIG. 1.
Figure 8:
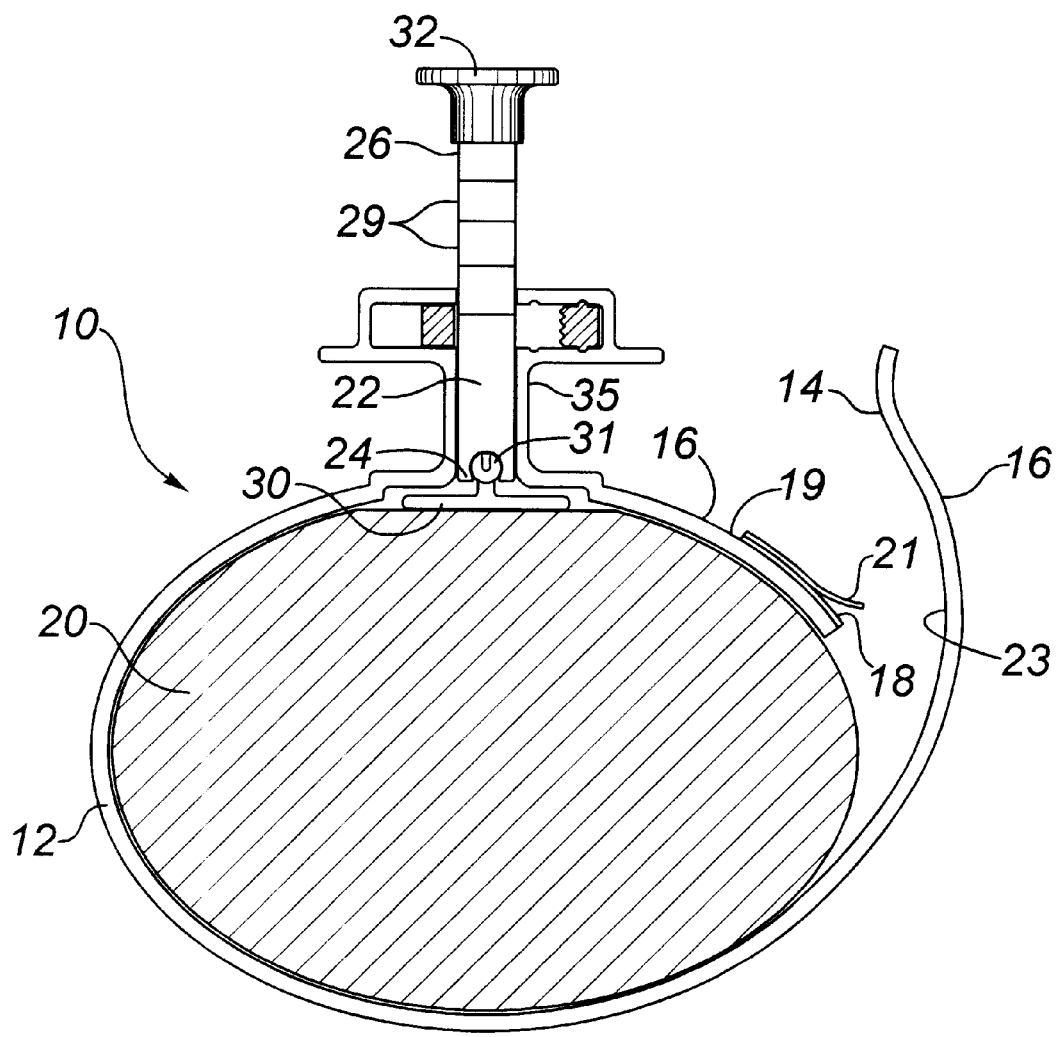
FIG. 8 is a front elevation view, in section, of the artery clamp illustrated in FIG. 1.

Referring to FIGS. 1 and 4, artery clamp 10 includes an inelastic girth band 12 having an interior face 14, and an exterior face 16. Referring to FIG. 7, an adhesive area 18 is placed on exterior face 16 adjacent a first end 19 of band 12. Referring to FIG. 8, adhesive area 18 is exposed by removal of tear-away strip 21. Referring to FIG. 7 when band 12 is overlapped, adhesive area 18 engages interior face 14 of band 12 thereby cinching band 12 about a limb 20. Referring to FIG. 8, an optional feature would be to also place an adhesive layer 23 on interior face 14 of band 12. The advantage of doing so would be that band 12 would adhere to the patient's skin and there would be less likelihood of an unwanted rotation of the band. The disadvantage of doing to would be that it would become of greater importance that band 12 be initially positioned in the desired position. Of course, without adhesive layer 23 band 12 may be rotated to the desired position after it is secured to the patients limb. Referring again to FIGS. 1 and 4, a plunger 22 extends through and is rotatable in relation to band 12. Plunger 22 has a first end 24 extending past interior face 14, a second end 26 extending past exterior face 16, and a helically threaded portion 28 positioned between first end 24 and second end 26. Referring to FIG. 8, A plurality of visual depth indicator markings 29 are positioned on plunger 22. Indicator markings 29 are colour coded to make them more visible against helically threaded portion 28. Referring to FIGS. 1, 4, and 8, a pressure member 30 is mounted on first end 24 of plunger 22. It is preferred that pressure member 30 have a pivotal mounting, such as swivel ball mounting 31 illustrated, in order to permit pressure member to conform to some degree to the contours of the body. A pressure adjustment knob 32 is positioned at second end 26 of plunger 22.

Referring to FIGS. 1 and 4, plunger 22 is supported by a tubular plunger housing 35. Plunger 42 extends through an elongate passage 34 in plunger housing 35. A first end 36 of plunger housing 35 is rigidly attached to a base 38 which is integrally incorporated into or secured to band 12. A second end 40 of wall 35 is rigidly attached to a locking member housing 42. Locking member housing 42 has a cavity 43 within which is contained a movable locking member 44. Locking member 44 has an elongate aperture 50 through which passes plunger 22. Locking member 44 is provided to engage threaded portion 28 thereby locking plunger 22 in a selected position relative to passage 34 and band 12, as will hereafter be described.

Figure 2:
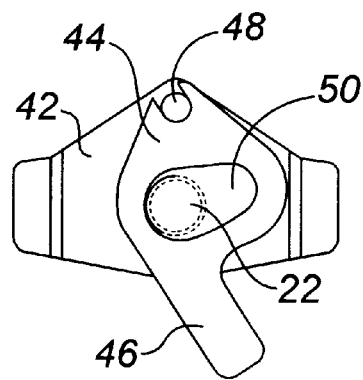
FIG. 2 is a top plan view, in section, of the locking member for the artery clamp illustrated in FIG. 1.
Figure 3:
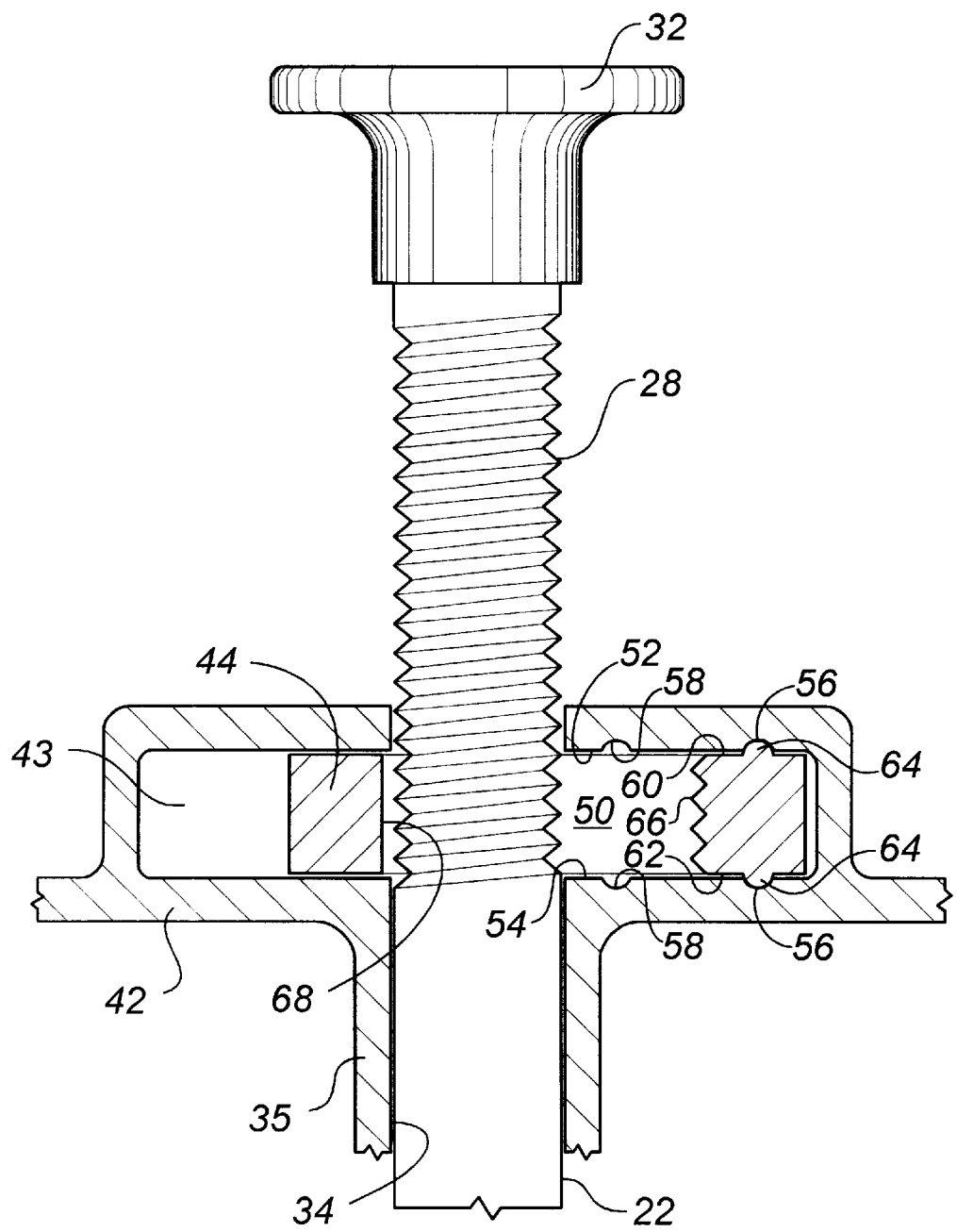
FIG. 3 is a detailed front elevation view, in section, of the locking member for the artery clamp illustrated in FIG. 1.
Figure 5:
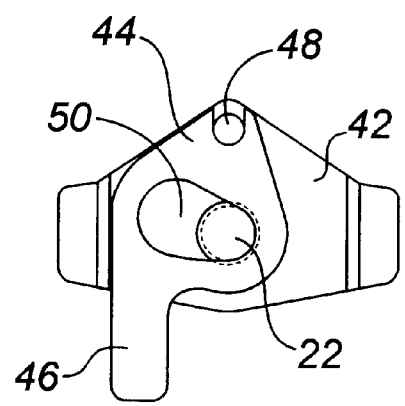
FIG. 5 is a top plan view, in section, of the locking member for the artery clamp illustrated in FIG. 4.
Figure 6:
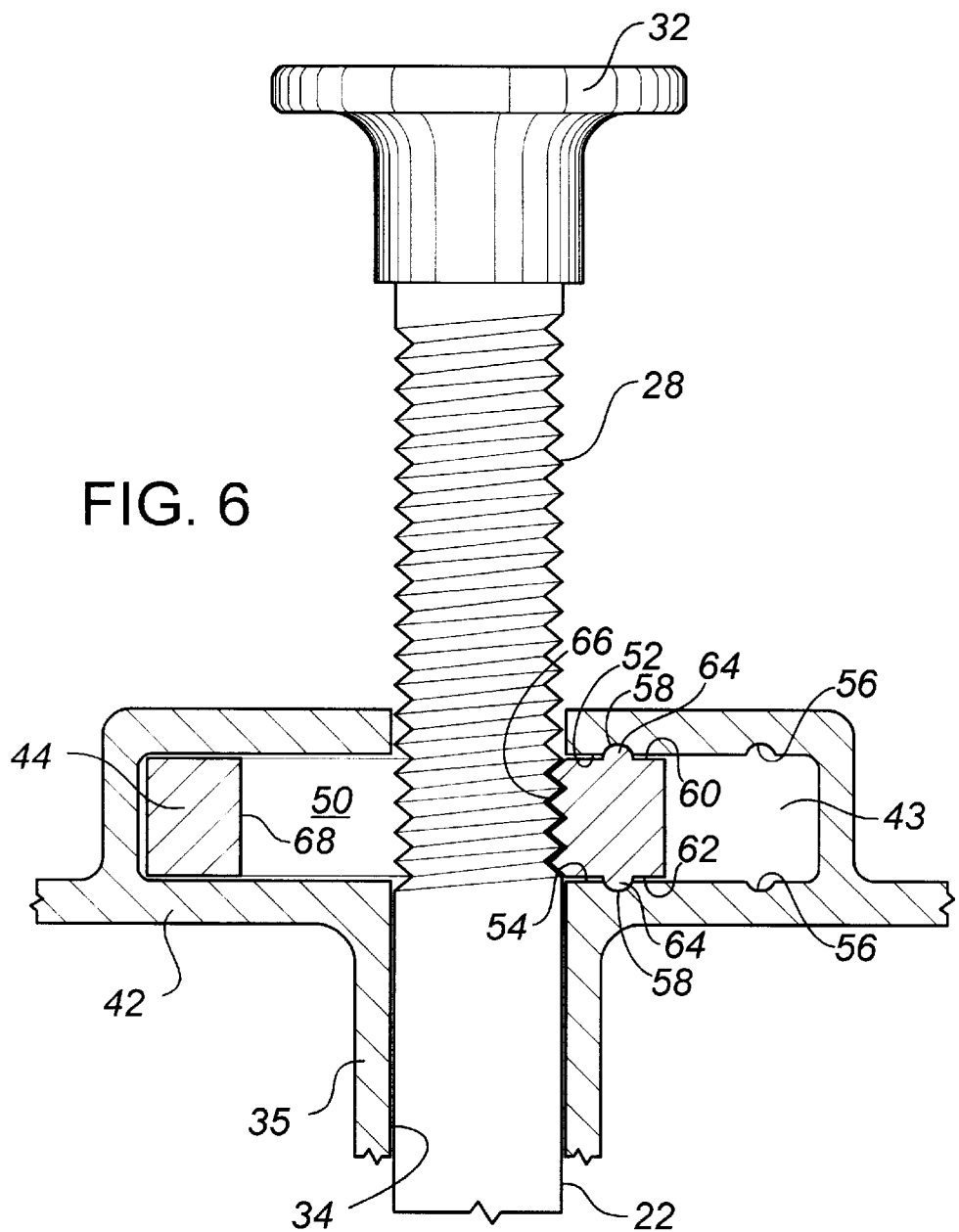
FIG. 6 is a detailed front elevation view, in section, of the locking member for the artery clamp illustrated in FIG. 4.

Referring to FIGS. 2 and 5, locking member 44 is pivotally attached within locking member housing 42 at a pivot point 48. Locking member 44 has a lever 46 whereby locking member 44 can be moved within housing 42 between a free position, as shown in FIG. 2, and an engaged position, as shown in FIG. 5. Referring to FIGS. 3 and 6, cavity 43 of housing 42 has a first or upper interior surface 52 and a second or lower interior surface 54. Each of first interior surface 52 and second interior surface 54 has a first engagement means in the form of a first locking groove 56 and a second engagement means in the form of a second locking groove 58. The body of locking member 44 has a first face 60 and a second face 62. Each of first face 60 and second face 62 has mating engagement means in the form of protecting ridges 64 adapted to mate with one of first locking groove 56 and second locking groove 58. Referring to FIG. 3, when locking member 44 is in the free position projecting ridges mate with first locking groove 56. Referring to FIG. 6, when locking member 44 is in the locking position, projecting ridges 64 mates with second locking groove 58. Referring again to FIGS. 3 and 6, aperture 50 has a first interior surface 66 and a second interior surface 68. First interior surface 66 is threaded to mate with threaded portion 28 of plunger 22.

Second interior surface 68 is smooth and does not engage threaded portion 28. Referring to FIG. 3, when locking member 44 is in a free position threaded surface 66 is spaced from plunger 22 thereby leaving plunger 22 free to move.

Referring to FIG. 6, when locking member 44 is in the engaged position threaded surface 66 engages threaded portion 28 thereby locking plunger 22 in position relative to passage 34 and band 12.

A preferred method of use of artery clamp 10 will now be described with reference to FIGS. 1 through 7. Referring to FIG. 8, Adhesive area 18 is exposed by removal of tear-away strip 21. Referring to FIG. 7, adhesive area 18 is then engaged with interior face 14, thereby cinching band 12 snugly about a limb 20, as illustrated in FIG. 1, without applying a compressive force. Artery clamp 10 is then oriented relative to limb 20 such that pressure member 30 is positioned to apply pressure on an artery. Locking member 44 is moved to the free position, illustrated in FIG. 2, and plunger 22 is depressed to apply pressure upon an artery of a patient, as illustrated in FIG. 3. Visual markings 29 are used to determine an initial depth to which plunger 22 is depressed. The pressure can then be further manually sensed by finger pressure upon plunger 22. Once the flow of blood through the artery has been stopped plunger 22 is locked in a selected position, illustrated in FIG. 4, by moving locking member 44 to the engaged position, illustrated in FIG. 5, in which threaded surface 66 of aperture 50 engages threaded portion 28 of plunger 22, as illustrated in FIG. 6. When locking member 44 is in the engaged position, a fine adjustment to pressure applied by pressure member 30 on limb 20 may be effected, as required, by using knob 32 to rotate plunger 22 in relation to locking member 44 along an inclined plane provided by helically threaded portion 28. When a surgical procedure has been completed and pressure on patient's artery is no longer required, the sections of band 12 connected by adhesive area 18 are separated and artery clamp 10 is removed from limb 20.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. An artery clamp, comprising:
    an inelastic girth bald having ani interior face and an exterior face;
    means for cinching the band about a limb;
    a plunger extending through the band and having a first end extending past the interior face and a second end extending past the exterior face;
    a pressure member mounted on the first end of the plunger;
    means for locking the plunger ill a selected position in relation to the band, wherein the means for locking the plunger in a selected position includes a movable locking member having a free position spaced from the plunger and leaving the plunger free to move and a locking position engaging the plunger and thereby lock the plunder in position.

2. The artery clamp as defined in claim 1, wherein the plunger is rotatable in relation to the band, the plunger having a helically threaded portion and the movable locking member having a threaded portion, the threaded portion of the movable locking member engaging the helically threaded portion of the plunger when in the locking position, fine pressure adjustment being effected by rotation of the plunger to move the plunger in relation to the movable locking member along an inclined plane provided by the helically threaded portion.

3. The artery clamp as defined in claim 1, wherein the movable locking member has a body with an elongate aperture through which the plunger extends, in the locking position a sidewall of the aperture of the movable locking body engaging the plunger.

4. The artery clamp as defined in claim 3, wherein a locking member housing is provided having a cavity with a first interior surface and a second interior surface, each of the first interior surface and the second interior surface having a first engagement means and a second engagement means, and the body of the locking member having a first face and a second face, each of the first face and the second face having mating engagement means adapted to mate with one of the first engagement means and the second engagement means, such that when the movable locking member is in the free position the mating engagement means mates with the first engagement means and when the movable locking member is in the locking position the mating engagement means mates with the second engagement means.

5. The artery clamp as defined in claim 1, wherein an adhesive area on the Exterior face of the band is covered by a tear away covering, the means for cinching the band about a limb being to tear away the tear away covering and overlap the band until an interior face of one portion of the band adheres to the adhesive area.

6. The artery clamp as defined in claim 1, wherein visual depth indicator markings are positioned on the plunger.

7. The artery clamp as defined in claim 1, wherein the pressure member is pivotally mounted to the plunger.

8. The artery clamp as defined in claim 1, wherein the interior face of the band has an adhesive layer, such that the interior face of the band adheres to a patient's limb.

9. An artery clamp, comprising:
    an inelastic girth band having an interior face and an exterior face;
    means for cinching the band about a limb;
    a plunger extending through and being rotatable in relation to the band and having a first end extending past the interior face, a second end extending past the exterior face, and a helically threaded portion positioned between the first end and the second end;
    a pressure member mounted on the first end of the plunger;
    a pressure adjustment knob positioned at the second end of the plunger;
    a movable locking member having a free position spaced from the plunger and leaving the plunger free to move and a locking position engaging the plunger and thereby lock the plunger in position, the movable locking member having a threaded portion, the threaded portion of the movable locking member engaging the helically threaded portion of the plunger when in the locking position, fine pressure adjustment being effected by rotation of the plunger to move the plunger in relation to the movable locking member along an inclined plane provided by the helically threaded portion.

10. The artery clamp as defined in claim 9, wherein the movable locking member has a body with an elongate aperture through which the plunger extends, in the locking position a sidewall of the aperture of the movable locking body engaging the plunger.

11. The artery clamp as defined in claim 9, wherein a locking member housing is provided having a cavity with a first interior surface and a second interior surface, each of the first interior surface and the second interior surface having a first engagement means and a second engagement means, and the body of the locking member having a first face and a second face, each of the first face and the second face having mating engagement means adapted to mate with one of the first engagement means and the second engagement means, such that when the movable locking member is in the free position the mating engagement means mates with the first engagement means and when the movable locking member is in the locking position the mating engagement means mates with the second engagement means.

12. The artery clamp as defined in claim 9, wherein an adhesive area on the exterior face of the band is covered by a tear away covering, the means for cinching the band about a limb being to tear away the tear away covering and overlap the band until an interior face of one portion of the band adheres to the adhesive area.

13. The artery clamp as defined in claim 9, wherein visual depth indicator markings are positioned on the plunger.

14. The artery clamp as defined in claim 9, wherein the pressure member is pivotally mounted to the plunger.

15. The artery clamp as defined in claim 9, wherein the interior face of the band has an adhesive layer, such that the interior face of the band adheres to a patient's limb.

* * * * *

UNITED STATES PATENT AND TRADEMARK OFFICE
CERTIFICATE OF CORRECTION

PATENT NO. : 6,068,646
DATED : May 30, 2000
INVENTOR(S) : A. Lam

It is certified that error appears in the above-identified patent and that said Letters Patent is hereby corrected as shown below:

Column 5,
Line 14 (Claim 1, line 13), "bald" should read -- band --
Line 14 (Claim 1, line 13), "ani" should read -- an --
Line 22, (Claim 1, line 9), "plunger;" should read -- plunger; and --
Line 23, (Claim 1, line 10), "ill" should read -- in --
Line 28, (Claim 1, line 15), "lock" should read -- locking --
Line 61, (Claim 5, line 2), "Exterior" should read -- exterior --.

Column 6,
Line 20, (Claim 9, line 13), "plunger;" should read -- plunger; and --
Line 24 (Claim 9, line 17), "lock" should read -- locking --.

Signed and Sealed this

Sixteenth Day of October, 2001

Attest:

NICHOLAS P. GODICI
Attesting Officer    Acting Director of the United States Patent and Trademark Office